United States Patent [19]

Wolf

[11] Patent Number: 5,739,159
[45] Date of Patent: Apr. 14, 1998

[54] MEDICAMENTS FOR THE TREATMENT OF CARDIAC INSUFFICIENCY

[76] Inventor: Horst Wolf, Im Tal 17, D-78476 Allensbach, Germany

[21] Appl. No.: 652,502

[22] PCT Filed: Nov. 24, 1994

[86] PCT No.: PCT/DE94/01395

§ 371 Date: May 31, 1996

§ 102(e) Date: May 31, 1996

[87] PCT Pub. No.: WO95/15161

PCT Pub. Date: Jun. 8, 1995

[30] Foreign Application Priority Data

Dec. 1, 1993 [DE] Germany ............... 43 40 879.6

[51] Int. Cl.$^6$ ............................... A61K 31/335
[52] U.S. Cl. ............................................. 514/475
[58] Field of Search ................................. 514/475

[56] References Cited

U.S. PATENT DOCUMENTS 4,946,866  8/1990  Wolf et al. ............... 514/475

FOREIGN PATENT DOCUMENTS

WO 87/00751  7/1986  WIPO.

OTHER PUBLICATIONS

Lapaschuk et al., "Response of Isolated Working Hearts to Fatty ...", *Circulation Research*, vol. 65, No. 2, (Aug. 1989), pp. 378–387.

Lopaschuk et al., "Glucose and Palmitate Oxidation in Isolated Working Rat Hearts ...", *Circulation Research*, vol. 66, No. 2 (1990), pp. 546–553.

Rupp et al., "Metabolically–Modulated Growth and Phenotype of the Rat Heart", *European Heart Journal*, vol. 13, Supplement D, (1992), pp. 56–61.

Tahiliani et al., "Diabetes–Induced Abnormalities in the Myocardium", *Life Sciences*, vol. 38, No. 11 (1986) pp. 959–974.

Bressler et al., "A Role of Fatty Acid Oxidation in Cardiac Hypertrophy", *Cardioscience*, vol. 4, No. 3 (Sep. 1993), pp. 133–142.

*Primary Examiner*—Phyllis G. Spivack
*Attorney, Agent, or Firm*—Evenson, McKeown, Edwards & Lenahan P.L.L.C.

[57] ABSTRACT

The use of oxirane carboxylic acids having the formula I:

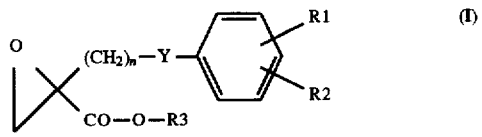

in which R1 and R2 are independently selected from hydrogen, halogen, straight-chain or branched 1–4C alkyl groups, straight-chain or branched 1–4C alkoxy groups, nitro or trifluoromethyl; R3 is hydrogen or straight-chain or branched 1–4C alkyl; Y is —O—$(CH_2)_m$—, where m is zero or a whole number from 1 to 4, and n is a whole number from 2 to 8, or a pharmaceutically acceptable salt thereof, is disclosed for treating heart insufficiency.

5 Claims, No Drawings

MEDICAMENTS FOR THE TREATMENT OF CARDIAC INSUFFICIENCY

This case is a 371 of PCT/DE94/01395 filed Nov. 24, 1994.

The invention relates to a new use of known oxirane carboxylic acids for the preparation of drugs for the treatment of cardiac insufficiency.

STATE OF THE ART

In European Patent Application No. EP-A-0 046 590, phen(alk) oxy-substituted oxirane carboxylic acids with a hypoglycemic and hypoketonemic activity, and in European Patent EP-A-0 231 365 phen(alk)oxy-substituted oxirane carboxylic acids with a hypocholesterolemic and hypotriglyceridemic activity, are described, which are to be used for the treatment of diabetes mellitus as well as diseases which are due to an elevated cholesterol and/or triglyceride concentration in the blood, such as coronary sclerosis and arteriosclerosis, as well as all associated disease variants which can be embraced under the general term "coronary heart diseases." The heart output and contractile force is limited in such diseases due to insufficient coronary blood supply, especially in diabetic hearts; coronary infarctions are often the result when local vessel blockage interrupts the heart's supply of nutrients and oxygen.

A heart muscle disease in the sense of a primary coronary insufficiency due to reduced performance of the heart muscle when there is no disturbance of the blood supply, does not exist in these cases.

A number of publications in scientific periodicals describe another characteristic of the known oxirane carboxylic acids, namely their ability to decrease intracellular acylcarnitine concentrations by inhibiting fatty acid oxidation, and by varying the acylcarnitine content in the muscle cell membranes, to affect the electro-physiological processes during heart contraction in the sense of an "anti-arrhythmic" activity (summarized in J.Clin.Invest.83, 1989, 917–936).

Some more recent works also report favorable effects of the known oxirane carboxylic acids on ischemic, hypoxic and diabetic hearts (summarized in G. D. Lopaschuk et al. in Current Concepts in Carnitine Research, 1992, 231–243) as well as a modifying action on the expression of the various myosine isoenzymes in rat hearts subjected to high blood-pressure rat hearts (H. Rupp et al., FASEB J. 6, 1992, 2349–2353; see also N. S. Dhalla et al., Molecul. Cellul. Biochem. 116, 1992, 3–9).

DESCRIPTION OF THE INVENTION

It has now been found that the known oxirane carboxylic acids disclosed in EP-A-0 046590 in human beings with dilative cardiomyopathy (cardiac insufficiency) vary the function of the contractile proteins such that a substantial improvement in heart performance is achieved. In particular, the use of the known oxirane carboxylic acids improves the cardiac output curve in patients with coronary insufficiency subjected to physical stress (stress ECG).

The subject matter of the invention is therefore the use of oxirane carboxylic acids of Formula I

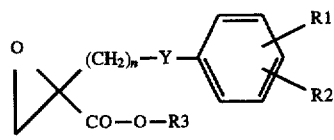

wherein

R1 represents a hydrogen atom, a halogen atom, a 1–4C alkyl group, a 1–4C alkoxy group, a nitro group or a trifluoromethyl group, R2 has one of the meanings of R1, R3 represents a hydrogen atom or a 1–4C alkyl group, Y represents the grouping —O—$(CH_2)_m$—, m is 0 or a whole number from 1 to 4, and n is a whole number from 2 to 8, whereby the sum of m and n is a whole number from 2 to 8, and of the pharmacologically acceptable salts of the carboxylic acids, for the preparation of medicaments for the prophylaxis and/or treatment of cardiac insufficiency.

The 1–4C alkyl groups can be straight-chain or branched alkyl moieties with 1 to 4 carbon atoms. Examples of straight-chain alkyl moieties are the methyl, ethyl, n-propyl and n-butyl moieties, of which the methyl and the ethyl moieties are preferred. Branched-chain alkyl moieties are, for example, the isopropyl, isobutyl, sec.-butyl and tert.-butyl moieties.

The alkyl moieties of 1–4C alkoxy groups can be either straight-chain or branched lower alkyl groups. The methoxy group is preferred as the 1–4C alkoxy group.

Halogen atoms are fluorine, chlorine and bromine atoms, of which fluorine, and especially chlorine, are preferred.

The substituents R1 and R2 of the phenyl ring are preferably in the meta or para position to the (alk) oxyalkylene oxirane carboxylic acid moiety.

The salts can be salts with inorganic and organic bases. As cations for the salt formation, the cations of the alkali metals, alkaline earth metals or earth metals are primarily used. Salts of lithium, sodium, potassium, magnesium, calcium and aluminum can be mentioned as examples.

The diseases can be any form of cardiac insufficiency. In connection with the present invention, cardiac insufficiency is to be understood as: idiopathic cardiac insufficiency, congestlye insufficiency (congestive failure) with and without dilation of the left ventricle, angina pectoris and the state following myocardial infarction, as well as all disease states associated therewith.

In the use of the compounds of formula I in accordance with the invention for the preparation of the above-named medicaments, the compounds of formula I (=active compounds) are used either as such, or preferably in combination with suitable pharmaceutical adjuvants or carriers in the form of tablets, dragees, capsules, suppositories, emulsions, suspensions or solutions, in which the active ingredient content is advantageously between 10 and 90%.

A soft gelatin capsule is considered to be an especially advantageous galenic formulation. In one particular embodiment the capsule contains a solution of the active ingredient in Miglyol 812 with an active substance content of 20.2%.

A skilled worker will know, based on his technical knowledge, which adjuvants or carriers are suitable for the desired medicament formulations. Besides solvents, gel formers, suppository bases, tabletting adjuvants and other active ingredient vehicles, it is possible to use, for example, antioxidants, dispersants, emulsifiers, antifoaming agents, taste masking agents, preservatives, solubilizers, coloring agents or especially permeation promoters and complexing agents (e.g. cyclodextrine).

The active substances can be administered orally or parenterally.

In general, it has proved advantageous in human medicine to administer the active substance or substances in oral administration in a daily dose of about 0.1 to about 30, preferably 0.3 to 15, and especially 0.6 to 3 mg/kg of body weight, optionally in the form of several, preferably 1 to 4 individual doses, in order to attain the desired result. In parenteral treatment, similar or (especially in the case of intravenous administration of the active substances) lower doses, as a rule, can be utilized. The determination of the optimal dose and manner of application of the active substance in any given case can easily be made by any skilled worker based on his professional knowledge.

If the active substances are to be used in treatment of the diseases mentioned above, then the medicaments obtained by the use according to the invention of the active substances can contain one or more other pharmacologically active compounds, especially other heart medications such as heart glycosides, nitro preparations, diuretics, ACE inhibitors, calcium antagonists, beta blockers, antihypertensives, vasodilators and minerals.

One embodiment of the invention is the use of oxirane carboxylic acids of Formula I, in which R1 and R2 are in the meta or para position, and R1 is a hydrogen atom, a chlorine atom, a methyl group, a methoxy group, a nitro group or a trifluoromethyl group, R2 is a hydrogen atom or a chlorine atom, R3 is a hydrogen atom or a 1–4C alkyl group, Y is the group —O—(CH$_2$)$_m$—, m is 0 or 1, and n is a whole number of 3 to 7, the sum of m and n being a whole number from 3 to 7, and the pharmacologically acceptable salts of the carboxylic acids, for the preparation of medicaments for the prevention and/or treatment of cardiac insufficiency.

Another embodiment of the invention is the use of oxirane carboxylic acids of Formula I, wherein R1 is in the meta or para position and R1 is a hydrogen atom, a chlorine atom or trifluoromethyl group, R2 is a hydrogen atom, R3 is a hydrogen atom, a methyl group or an ethyl group, Y is the grouping —O' n is a whole number from 4 to 6, and the pharmacologically acceptable salts of the carboxylic acids, for the preparation of medicaments for the prevention and/or treatment of cardiac insufficiency.

A preferred embodiment of the invention is the use of one or more oxirane carboxylic acids selected from the group consisting of:

2-(4-(3-chlorophenoxy)-butyl)-oxirane-2-carboxylic acid ethyl ester, 2-(4-(3-trifluoromethylphenoxy)-butyl)-oxirane-2-carboxylic acid ethyl ester, 2-(6-4-chlorophenoxy)-hexyl)-oxirane-2-carboxylic acid ethyl ester, 2-(5-(4-chlorophenoxy)-pentyl)-oxirane-2-carboxylic acid ethyl ester, 2-(6-(3,4-dichlorophenoxy)-hexyl)-oxirane-2-carboxylic acid ethyl ester, 2-(6-(4-fluorophenoxy)-hexyl)-oxirane-2-carboxylic acid ethyl ester, and 2-(6-phenoxyhexyl)-oxirane-2-carboxylic acid ethyl ester, as well as the corresponding oxirane carboxylic acids and their pharmacologically acceptable salts, for the preparation of medicaments for the prevention and/or treatment of cardiac insufficiency.

An especially preferred embodiment of the invention is the use of the (+) enantiomer of 2-(6-(4-chlorophenoxy)-hexyl)-oxirane-2-carboxylic acid ethyl ester for the preparation of medicaments for the prevention and/or treatment of cardiac insufficiency.

I claim:

1. A method of treating a condition of deteriorated heart muscle function under unimpeded blood flow, said method comprising administering to a patient suffering from said condition an effective heart muscle function improving amount of an oxirane carboxylic acid compound corresponding to the Formula I:

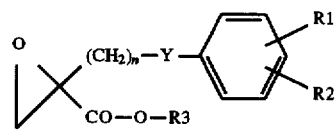

wherein

R1 is a hydrogen atom, a halogen atom, a straight-chain or branched 1–4C alkyl group, a straight-chain or branched 1–4C alkoxy group, a nitro group or a trifluoromethyl group, R2 has one of the meanings of R1, R3 is a hydrogen atom or a straight-chain or branched 1–4C alkyl group, Y is the group —O—(CH$_2$)$_m$—, m is zero or a whole number from 1 to 4, and n is a whole number from 2 to 8, whereby the sum of m and n is a whole number from 2 to 8, or a pharmacologically acceptable salt thereof.

2. A method according to claim 1, wherein R1 and R2 are in the meta or para position; R1 is a hydrogen atom, a chlorine atom, a methyl group, a methoxy group, a nitro group or a trifluoromethyl group; R2 is a hydrogen atom or a chlorine atom; R3 is a hydrogen atom or a 1–4C alkyl group; Y is the grouping —O—(CH$_2$)$_m$— in which m is zero or 1; n is a whole number from 3 to 7, and the sum of m and n is a whole number from 3 to 7.

3. A method according to claim 1, wherein R1 is in the meta or para position, and R1 is a hydrogen atom, a chlorine atom or trifluoromethyl group; R2 is a hydrogen atom; R3 is a hydrogen atom, a methyl group or an ethyl group; Y is the grouping —O—, and n is a whole number from 4 to 6.

4. A method according to claim 1, wherein said compound comprises at least one oxirane carboxylic acid selected from the group consisting of:

2-(4-(3-chlorophenoxy)-butyl)-oxirane-2-carboxylic acid ethyl ester, 2-(4-(3-trifluoromethylphenoxy)-butyl)-oxirane-2-carboxylic acid ethyl ester, 2-(6-(4-chlorophenoxy)-hexyl)-oxirane-2-carboxylic acid ethyl ester, 2-(5-(4-chlorophenoxy)-pentyl)-oxirane-2-carboxylic acid ethyl ester, 2-(6-(3,4-dichlorophenoxy)-hexyl)-oxirane-2-carboxylic acid ethyl ester, 2-(6-(4-fluorophenoxy)-hexyl)-oxirane-2-carboxylic acid ethyl ester, and 2-(6-phenoxyhexyl)-oxirane-2-carboxylic acid ethyl ester, the corresponding oxirane carboxylic acids, and their pharmacologically acceptable salts.

5. A method according to claim 1, wherein said compound comprises the (+) enantiomer of 2-(6-(4-chlorophenoxy)-hexyl)-oxirane-2-carboxylic acid ethyl ester.

* * * * *